United States Patent [19]
Brown et al.

[11] Patent Number: 5,466,216
[45] Date of Patent: Nov. 14, 1995

[54] ANTEGRADE/RETROGRADE CARDIOPLEGIA METHOD AND SYSTEM

[75] Inventors: Jack W. Brown, Santa Ana; Brian Strauss, Mission Viejo; George W. White, Lake Forest, all of Calif.

[73] Assignee: Gish Biomedical, Inc., Irvine, Calif.

[21] Appl. No.: 225,586

[22] Filed: Apr. 11, 1994

[51] Int. Cl.$^6$ .............................. A61M 1/00; A61M 5/00
[52] U.S. Cl. ....................... 604/33; 604/249; 128/DIG. 3
[58] Field of Search ................................ 604/4–6, 28, 30, 604/32, 33, 248, 249; 128/DIG. 3; 251/319, 324, 325

[56] References Cited

U.S. PATENT DOCUMENTS

| | | | |
|---|---|---|---|
| 2,985,566 | 5/1961 | Tsien et al. | 251/324 |
| 3,044,491 | 7/1962 | Sangster | 251/324 |
| 3,407,748 | 10/1968 | Mamo | 604/4 |
| 3,678,959 | 7/1972 | Liposky | 251/325 |
| 3,859,985 | 1/1975 | Eckhart | 604/4 |
| 4,193,406 | 3/1980 | Jinotti | 604/33 |
| 4,401,431 | 8/1983 | Arp | 604/4 |
| 4,529,397 | 7/1985 | Hennemuth et al. | 604/4 |
| 4,708,713 | 11/1987 | Lentz | 604/5 |
| 4,756,705 | 7/1988 | Beijbom et al. | 604/4 |
| 4,883,455 | 11/1989 | Leonard | 604/4 |
| 5,011,469 | 4/1991 | Buckberg et al. | 604/4 |
| 5,247,966 | 9/1993 | Stevens et al. | 604/249 |
| 5,322,500 | 6/1994 | Johnson et al. | 604/4 |

OTHER PUBLICATIONS

Gish Biomedical, Inc., Gish Cardioplegia brochure, Apr. 1984.

DPL Inc., ARISS Antegrade/Retrograde Integral Selector Switch Directions for Use, 1991.

DLP, Inc., ARISS Switch Information for Use, 1990.

The Journal of Extra–Corporeal Technology, Karim Jabar et al, Continuous Warm Blood Cardioplegia, Fall 1990, pp. 107–109.

Journal of Cardiac Surgery, G. Buckberg, M.D., Antegrade/Retrograde Blood Cardioplegia to Ensure Cardioplegic Distribution: Operative Techniques and Objectives, 1989, pp. 216–238.

Gish Biomedical, Inc., The Gish CPS Plus Recirculating Cardioplegia System Brochure, 1992.

*Primary Examiner*—C. Fred Rosenbaum
*Assistant Examiner*—Frank Wilkens, III
*Attorney, Agent, or Firm*—George F. Bethel; Patience K. Bethel

[57] ABSTRACT

An antegrade/retrograde cardioplegia valve, system and method are provided. The valve includes conduits for entry of blood and cardioplegic solution, for pressure sensing, and for delivery of blood and cardioplegic solution to the aortic root by means of an aortic root cannula for antegrade infusion or to the coronary sinus by means of a coronary sinus cannula for retrograde infusion. Within the valve a cylindrical sliding member slides axially within an inner cylindrical chamber for selection of retrograde or antegrade infusion. An independent conduit communicates with the coronary sinus cannula for continuous coronary sinus pressure monitoring. A method and system incorporating the valve are also provided.

19 Claims, 4 Drawing Sheets

5,466,216

ANTEGRADE/RETROGRADE CARDIOPLEGIA METHOD AND SYSTEM

FIELD OF THE INVENTION

This invention relates to the field of open heart surgery and particularly to a valve, system and method for delivery of cardioplegia solution to the heart.

BACKGROUND OF THE INVENTION

During open heart surgery, the heart muscle or myocardium requires vital oxygen and energy supplements during the surgical procedure to prevent deterioration of the myocardium. In order for the surgeon to work on the heart, it must be stopped. This is accomplished by means of a cardioplegic solution or crystalloid which contains potassium chloride (KCL) in an aqueous solution which interferes with the electrical activity of the myocardium on a cellular level. Crystalloid defines a substance that forms a true solution, in solution diffuses readily through a membrane, and is capable of being crystallized.

In cardiovascular bypass, blood from the vena cava of a patient undergoing coronary surgery is sent to a venous reservoir and is passed through an oxygenator or artificial lung where it is mixed with oxygen. A major portion of this oxygenated blood is filtered and returned to the patient for circulation throughout the body to be returned again and gathered from the vena cava.

In order to initiate cardioplegia, a minor portion of the oxygenated blood is withdrawn from the oxygenator and is then mixed in specific ratios with the potassium chloride cardioplegic solution. The mixture is then passed through a heat exchanger mixing device. Then the mixture is intermittently or continuously perfused to the myocardium, usually via the aortic root or the coronary sinus. In some instances, all blood or all cardioplegic solution is perfused to the heart. Blood and cardioplegic solution that seeps out of the left ventricle and surrounding tissue is collected from the chest or pleural area for reuse. There are several suction devices which collect the blood and other fluids from the pleura. If the blood is of high quality it is sent to the venous reservoir for filtration and oxygenation. If the blood is of good quality but is dilute or is mixed with cardioplegia solution, it is suctioned off to a cell saver which operates like a centrifuge to separate the good quality blood cells from the excess cardioplegic solution for reuse.

There are two main types of cardioplegia: cold cardioplegia and warm cardioplegia, the choice of which is determined by the surgeon depending upon the condition of the patient and the type of surgery.

Cold cardioplegia utilizes a cold (about 4°–12° C.) cardioplegic solution comprised of 100% crystalloid solution or a mixture of cardioplegic solution and blood with hypothermia to reduce the energy required by the heart. The solution or mixture is infused intermittently or continuously throughout the cardiac surgery.

Warm cardioplegia utilizes a mixture of oxygenated blood and a cardioplegic solution at a temperature of about 20°–37° C. The mixture is infused continuously or intermittently throughout the cardiac surgery.

Using cold or warm cardioplegia, the mixture of the blood and the cardioplegic solution is carefully controlled. Normally, there is a 4 to 1 ratio of blood to cardioplegic solution although ratios of 1 to 1, 2 to 1, and 9 to 1 ratio are sometimes used. The ratio can be controlled by the diameter of the tubing used to carry the blood (typically ¼ inch diameter tubing) and the diameter of the tubing used to carry the cardioplegic solution (typically ⅛ inch diameter tubing). The maximum ratio of blood to cardioplegic solution is then partially fixed by the diameter of the tubing.

The fixed ratio of the blood to the cardioplegic solution maintains a constant amount of potassium given to the heart. This can result in potassium overloading which is thought to cause damage to the myocardium. In order to overcome this problem, two or more separate bags of cardioplegic solution can be used which contain different concentrations of potassium. One bag having a high concentration of potassium is used to arrest the heart and the other bag containing a lesser concentration of potassium is used to maintain the heart.

The two or more separate sources or bags of cardioplegic solution are connected to a Y fitting. A clamping means permits the selection of one or the other bag of cardioplegic solution for mixture with blood.

The two respective tubing lines containing the cardioplegic solution and the blood are passed in parallel through a pump such as a roller pump. The two respective tubing lines then pass through a mixing device having a single exit line. The pump delivers the mixture at a specific preset flow rate to the antegrade/retrograde valve of the invention for infusion to the heart.

Infusion is normally conducted at a relatively high flow rate to the aortic root (antegrade infusion) to arrest the heart. Alternate infusion is made at a lower flow rate to the coronary sinus (retrograde infusion) and to the aortic root thereafter.

Cardioplegic solution consists of aqueous solutions of potassium chloride and often contains additional ingredients such as dextrose, glutamate, aspartate, and various other electrolytes such as $Ca^{+2}$ and $Mg^{+2}$. Cardioplegic solutions are delivered by alternating between antegrade cardioplegia and retrograde cardioplegia containing high and low potassium concentrations.

In order to arrest the heart and to limit the total cardioplegia volume, typically antegrade cardioplegia is given first to the aortic root to supply approximately 20 mEq/L of potassium given at 300–350 ml/min for 2 minutes to stop the heart. Thereafter, retrograde cardioplegia is delivered to the coronary sinus at 100–200 ml/min to supply approximately 10 mEq/L of potassium for about 2 minutes. In this instance, the concentration of potassium is controlled through the flow rate.

Alternately, the high concentration potassium chloride cardioplegic solution can be infused antegrade to arrest the heart. Then, the low potassium cardioplegic solution can be infused to deliver the balance of the potassium.

Thereafter, reinfusions during surgery are divided between 1 minute antegrade and 1 minute retrograde at approximately 20 minute intervals. Reinfusions can also be delivered continuously.

Warm reinfusion is often given prior to restarting the heart. For example, warm reinfusion is delivered at 150 ml/min for 3–5 minutes which is divided between antegrade and retrograde to limit reinfusion injury. Other combinations of cold and warm cardioplegia are utilized depending upon the individual surgeon and the condition of the patient. This invention should not be limited by the various combinations of delivery of cardioplegia used.

Antegrade pressure at the aortic root should be maintained at less than about 300 mm Hg pressure and retrograde pressure at the coronary sinus should be maintained at less than about 50 mm Hg pressure to avoid myocardial edema and hemorrhage. The significant pressure differential requires accurate pressure reading and control. In addition, it is necessary to ensure that the proper pressure is delivered to the aortic root or to the coronary sinus to avoid damage to the heart. Pressure can be controlled by adjustment of the flow rate of the pump. Similarly, the temperature must be monitored and controlled.

Since the antegrade cardioplegic solution and the retrograde cardioplegic solution are introduced into different parts of the heart at different times, two lines or tubes are required. The two lines are connected to a roller or other type of pump. One of the lines must be clamped or otherwise restricted while the other is in operation.

One device which has been used in the past to stop the flow in one line while permitting flow in the other line is in the form of a three way stopcock which selectively permits flow through one or both lines depending on its position.

The three way stopcock device requires two hands for operation making it inconvenient to operate. The stopcock is connected to PVC tubing which gives good visibility but kinking and leaks of the tubing have been experienced. Also, there is possible pressurization of the coronary sinus via communication with the antegrade pressure monitoring line.

Another device utilizes a rotary compression switch and silicone rubber delivery lines. Both lines pass through a housing, one on either side of a circular rotation member which selectively compresses or releases one or both lines depending upon the position of rotation. Thus, both lines can be unclamped in order to prime the lines, and then one line clamped to permit selective flow in the other line, or both lines can be clamped to prevent flow through either line.

There are several disadvantages to the use of the rotary clamping switch. One disadvantage is that two hands must be used to change the position of the switch.

In addition, the network of delivery and pressure lines are easily tangled causing confusion. Moreover, the silicone rubber tubing offers poor visibility for priming.

The above disadvantages are eliminated by the system, valve, and method of the invention.

Thus, it is an object of the invention to provide an antegrade/retrograde method, valve and system which utilizes large bore ⅛" clear PVC tubing with large bore ⅛" Luer connectors. Coextruded PVC tubing is easy to handle reducing tangling and confusion during use. The clarity of the tubing offers good visibility for priming and other visual monitoring of the tubing adding to the safety during use. If desired, color coding can be added for further convenience.

It is another object of the invention to provide an antegrade/retrograde cardioplegia method, system, and valve which facilitates pressure monitoring by a method and valve having two large bore stopcocks. Separate antegrade and retrograde pressure lines provide simultaneous antegrade/retrograde pressure monitoring. Connectors are provided for measurement of aortic root and coronary sinus pressures.

It is another object of the invention to provide an antegrade/retrograde cardioplegia method and system which combines large bore tubing and connectors to reduce pressure drop and blood hemolysis (dissolution or breakdown of red corpuscles with liberation of their hemoglobin). The ergonomically designed valve can be operated with one hand to deliver cardioplegic solution to the aortic root via antegrade flow or to the coronary sinus via retrograde flow. This feature eliminates the need to anchor the valve to the table. Also, the ergonomic design of the valve provides a natural fit to the hand which allows stability when used in different positions and allows for flexible control and movement in the surgical field.

SUMMARY OF THE INVENTION

An antegrade/retrograde cardioplegia delivery method and system are provided by the invention. The system comprises in combination at least one reservoir for cardioplegic solution, at least one reservoir for blood, flow control means, pump means, mixing means for mixing cardioplegic solution and blood, heat exchange means for heating or cooling cardioplegic solution and blood, a novel antegrade/retrograde valve, aortic root cannula means, coronary sinus cannula means, aortic root pressure sensing means, coronary sinus pressure sensing means, at least one tubing means for fluid communication between the reservoir means, pump means, mixing means, heat exchange means, and the antegrade/retrograde valve and at least one tubing means for fluid communication between the antegrade/retrograde valve and the aortic root cannula means and the coronary sinus cannula means.

The novel antegrade/retrograde valve of the invention comprises a housing having an inner chamber. At least one conduit is in communication with the inner chamber and with a mixing means for introduction of cardioplegic solution and blood mixture into the inner chamber. At least one second conduit is in communication with the inner chamber for communication with an aortic root pressure sensing means.

At least one third conduit is in communication with the inner chamber for communication with an aortic root cannula. At least one fourth conduit is in communication with the inner chamber for communication with a coronary sinus cannula.

A sliding member is disposed for sliding within the inner chamber. One position enables selective fluid communication between the first conduit, the second conduit, and the third conduit for antegrade infusion and antegrade or aortic root pressure monitoring. Another position enables selective fluid communication between the first conduit and the fourth conduit for retrograde infusion.

A separate retrograde pressure sensing conduit or tube communicates with the coronary sinus cannula and with a pressure sensor or transducer and a retrograde pressure meter or monitor to provide continuous retrograde pressure or coronary sinus pressure measurement. The retrograde or coronary sinus pressure sensing conduit is secured to the valve housing but is operatively independent of the valve.

The method of the invention comprises providing at least one cardioplegic solution, collecting or providing oxygenated blood, mixing at least one cardioplegic solution with the oxygenated blood to provide a mixture having predetermined ratios of blood to cardioplegic solution which can range from all blood to all cardioplegic solution, delivering the mixture through the invention valve selected for antegrade or for retrograde infusion, cannulating the aortic root and connecting the cannula to the valve for antegrade infusion, cannulating the coronary sinus and connecting the cannula to the valve for retrograde infusion, measuring and monitoring the aortic root or antegrade infusion pressure when said antegrade infusion is taking place and measuring and monitoring the coronary sinus or retrograde infusion pressure at least when retrograde infusion is taking place.

The invention will be more readily understood by reference to the attached drawings and the following description.

DETAILED DESCRIPTION OF THE DRAWINGS

Figure 7:
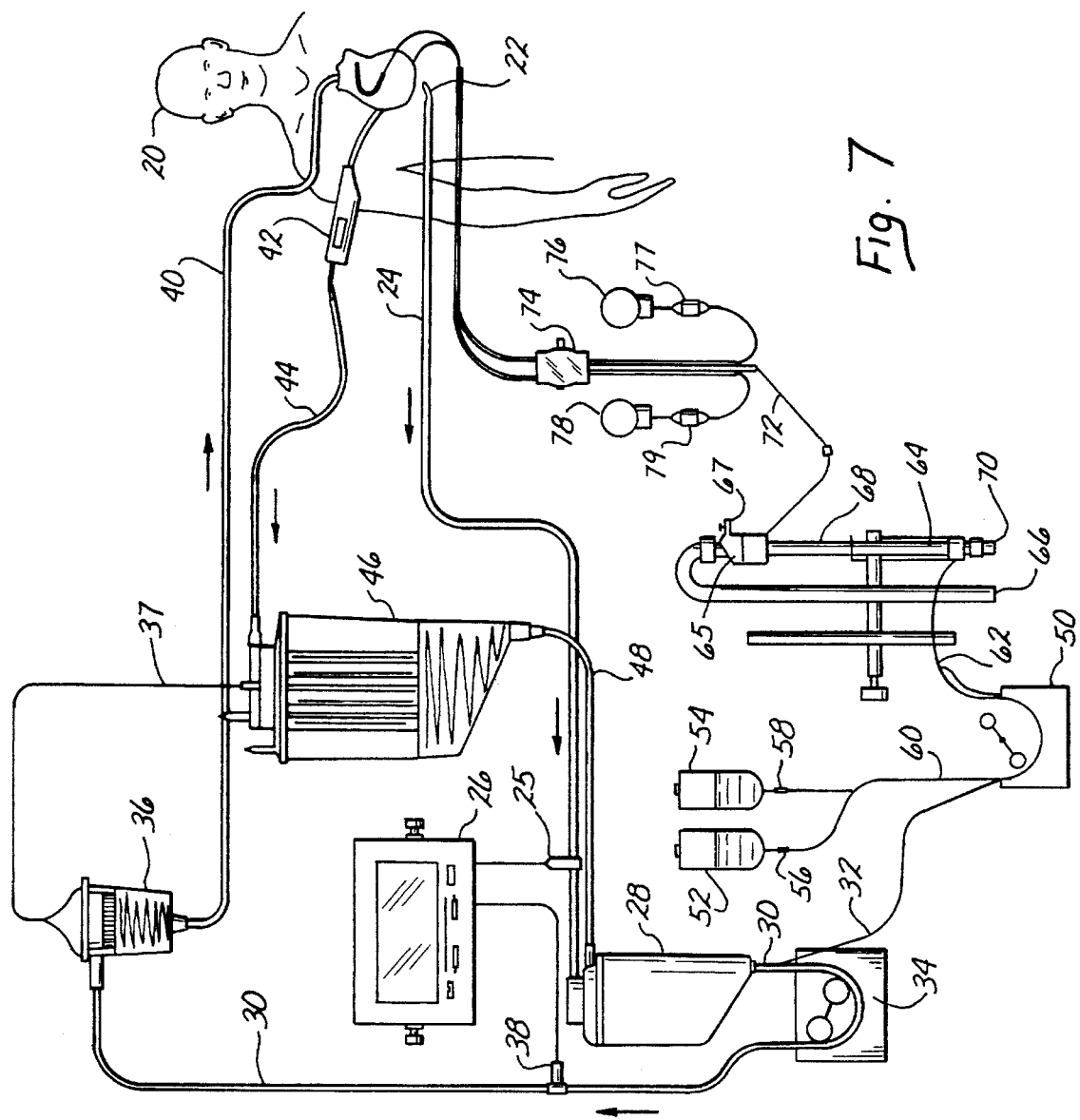
FIG. 7 shows a schematic diagram of a cardiovascular bypass circuit utilizing the antegrade/retrograde valve of FIGS. 1–6.

FIG. 7 shows an overall schematic diagram of the cardiovascular bypass circuit which utilizes the valve of the invention. A patient 20 who is undergoing bypass surgery has his venous blood withdrawn from his vena cava as indicated at 22 through line or tube 24 which has an inline connection 25 to a blood oxygen saturation measuring and charting device 26. The blood passing through line 24 is directed to an oxygenator 28 which adds oxygen to the venous blood and removes carbon dioxide from the venous blood to replace the function of the lungs during surgery.

Oxygenated blood leaves the oxygenator 28 through line 30 where a minor portion of the oxygenated blood is diverted through line 32. The main portion of the blood continues to flow through line 30 to a pump 34. Pump 34 pumps the blood to an arterial filter 36, and the effectiveness of the oxygenator is measured by an inline connection 38 to the blood oxygen saturation measuring and charting device 26.

At the arterial filter 36, particulate matter and micro-air emboli from the blood are removed and the filtered blood is returned to the body of the patient 20 through line 40 for circulation throughout the body to be returned again and gathered from the vena cava.

At the same time, blood lost from the patient's circulatory system during the operation is suctioned out of the chest or pleural cavity by means of suction wands indicated at 42. The blood is directed through line 44 to a cardiotomy reservoir 46. In the cardiotomy reservoir 46, the blood is defoamed and filtered and withdrawn through line 48 where it enters the oxygenator 28 to be returned to the patient 20 in the manner previously described.

Line 37 between the arterial filter 36 and the cardiotomy reservoir 46 diverts a small flow of blood from filter 36 and returns it to the cardiotomy reservoir 46 to remove any air bubbles that may collect in the filter 36.

The system just described provides the function of the heart and lungs with respect to the body circulation.

The demands and needs of the heart muscle are supplied by a different route. As shown at the oxygenator 28, the line 30 has a smaller line 32 which contains oxygenated blood which is passed through a pump 50. At the same time a cardioplegic solution from a reservoir 52 or 54 having flow control clamps 56 and 58 can be selectively clamped or unclamped for entry into line 60 which also passes through pump 50.

The blood line or tube 32 and the cardioplegic solution line or tube 60 are joined downstream of the pump 50 to form a single line or tube 62 which passes into a combination heat exchanger/mixer 64. The heat exchanger/mixer 64 is heated or cooled by circulation of water through an inlet port 66 which passes through a heat exchange element 68 to exit through water outlet port 70.

The heat exchanger/mixer 64 includes a bubble chamber 65 with a stopcock 67 for venting.

The cardioplegic solution and blood entering from line 62 pass in exterior contact with the heating element 68 for mixing and heating or cooling prior to exiting through line 72.

Here, the mixture of cardioplegic solution and blood passes through a valve 74 of the invention which is an antegrade/retrograde valve having tubular or line connections for fluid communication with the aortic root of the heart of a patient 20 for antegrade infusion or for fluid communication with the coronary sinus of the heart of a patient 20 for retrograde infusion. Pressure measurement can be monitored and read during antegrade and retrograde infusion through pressure sensors or pressure transducers 77 and 79 which connect with pressure meters 76 and 78.

The cardioplegic delivery system which mixes cardioplegic solution and blood reduces the heart's metabolism and acts to prevent damage to the heart muscle during surgery.

The actual composition of the cardioplegic solution is a matter of preference by the surgeon. It is mainly an aqueous solution including KCl and other electrolyte solutions providing, for example, calcium or magnesium and sometimes contains glutamate, aspartate and other ingredients thought to nourish the heart.

Examples of typical cardioplegic solutions are given below. These solutions are given as Examples only and are not intended to limit the scope of this invention.

An example of a high potassium cardioplegic solution consists of 560 ml of 5% dextrose in water, 50 ml of CPD solution, 30 ml of 2 mEq/ml of KCl, 200 ml of 0.3% (tris(trihydroxymethyl)aminomethane, with a pH 7.8 and an Osmolality of 350 mOsm.

Another example of a high potassium cardioplegic solution known as High Potassium Fremes' solution consists of 1,000 ml of 5% dextrose in water, 18 mEq $MgSO_3$, 100 mlq of KCl, 12 mEq tromethamine, and 20 ml of CPD solution; with an osmolality of 425 mOsm/l and pH 7.95.

An example of a low potassium cardioplegic solution consists of 560 ml of 5% dextrose in water, 50 ml of CPD solution, 10 ml of 2 mEq/ml of KCl, 200 ml of 0.3% (tris(trihydroxymethyl)aminomethane, with a pH 7.8 and an osmolality of 350 mOsm.

Another example of a low potassium solution known as Low Potassium Fremes' solution consists of 1,000 ml of D5W, 25 mEq of KCl, 18 mEq of $MgSO_3$, 12 mEq of THAM, and 20 ml of CPD solution.

An example of a cardioplegic solution for warm infusion consists of 225 ml of 5% dextrose in water, 40 ml of 50% dextrose in water, 225 ml of CPD solution, 30 ml of 2 mEq/ml of KCl, 225 ml of 0.3% (tris(trihydroxymethyl)aminomethane, 250 ml of aspartate, and 250 ml of glutamate, with a pH 7.6 and an osmolality of 390 mOsm.

Figures 1, 2:
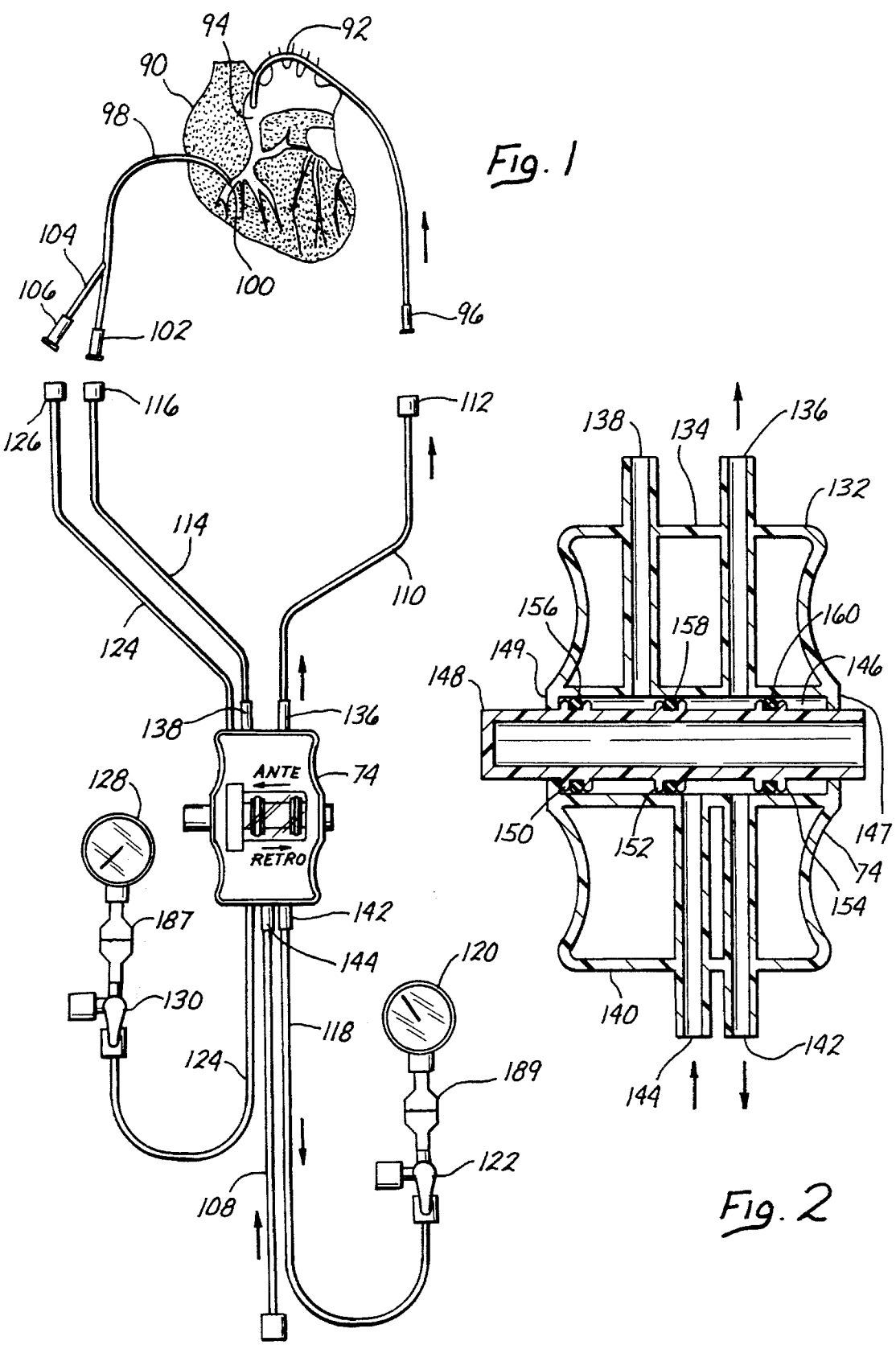
FIG. 1 shows a schematic representation of the antegrade/retrograde valve of the invention selected for antegrade infusion through an aortic root cannula and aortic root or antegrade pressure measurement.
FIG. 2 shows an enlarged section of the antegrade/retrograde valve of the invention as shown in FIG. 1 selected for antegrade infusion and aortic root or antegrade pressure measurement.
Figures 3, 4:
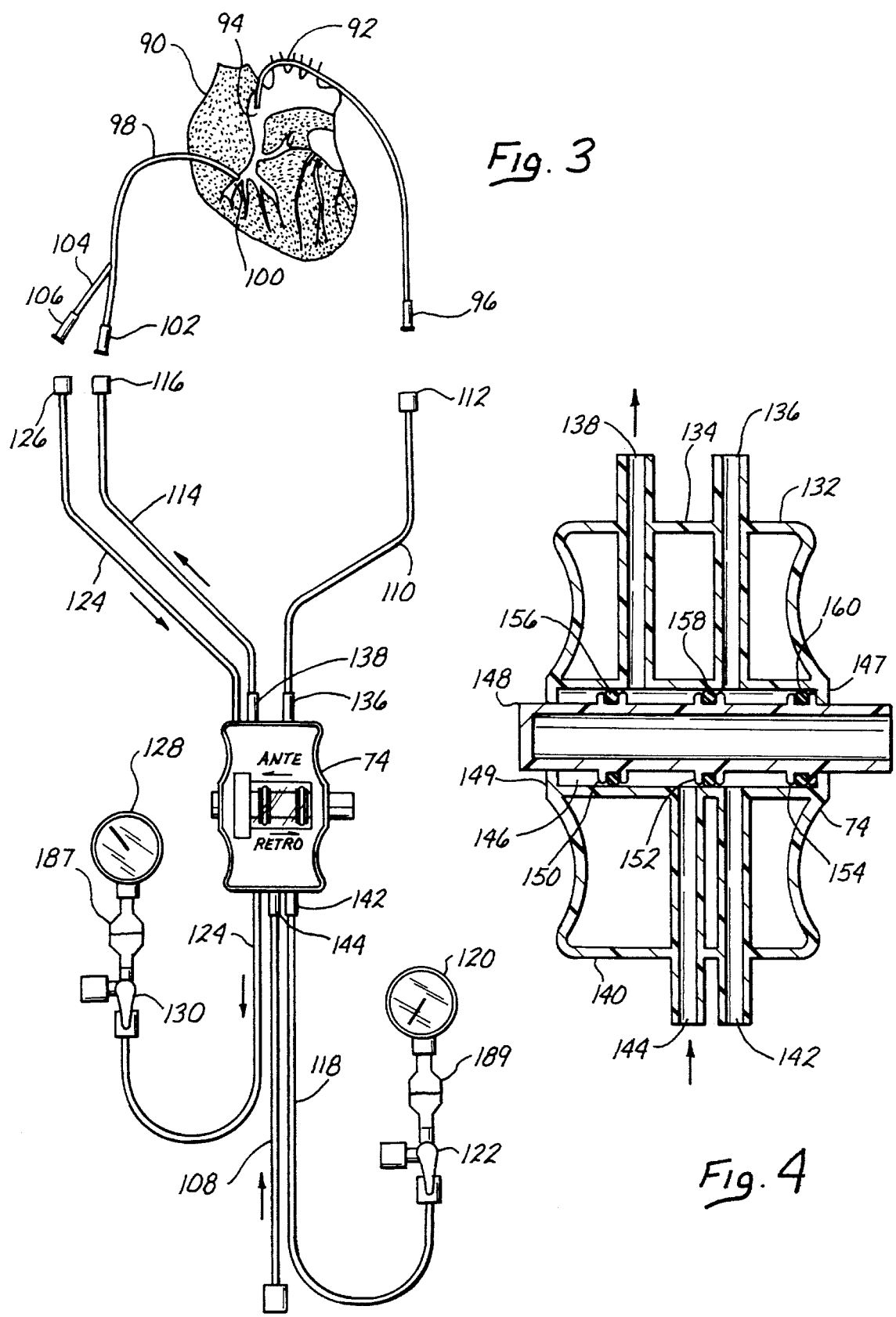
FIG. 3 shows a schematic representation of the antegrade/retrograde valve of the invention selected for retrograde infusion through the coronary sinus and having coronary sinus or retrograde pressure measurement through the coronary sinus cannula.
FIG. 4 shows an enlarged section of the antegrade/retrograde valve of the invention as shown in FIG. 3 selected for retrograde infusion and coronary sinus or retrograde pressure measurement.

The operation of the antegrade/retrograde valve 74 of the invention is shown in FIGS. 1–6. Portions of the connections are shown separated for purposes of illustration. FIGS. 1 and 2 show a set-up for antegrade infusion and FIGS. 3 and 4 show a set-up for retrograde infusion using the antegrade/retrograde valve 74 of the invention.

As seen in FIGS. 1 and 3, a heart 90 of a patient has inserted an aortic root cannula 92 into the aortic root 94 of the heart 90. The aortic root cannula 92, also known as an antegrade cannula, is provided with a Luer connection 96. Similarly, a coronary sinus cannula 98, which is also called a retrograde cannula, is inserted into the coronary sinus 100 of the heart 90. The retrograde cannula 98 is provided with a Luer connection 102 and a small side line 104 having a Luer connection 106.

The antegrade cannula 92 can be connected to valve 74 through tube 136 and line 110 through Luer connectors 96 and 112. Retrograde cannula 98 can be connected to valve 74 through tube 138, and line 114 through Luer connectors 102 and 116.

A mixture of blood and cardioplegic solution enters line 108 of valve 74. When valve 74 is in the position shown in FIG. 2, the mixture is directed to line 110 through Luer connectors 112 and 96 to cannula 92 for antegrade flow.

When valve 74 is in the position shown in FIG. 4 for retrograde infusion, the mixture of blood and cardioplegic solution from line 108 enters valve 74 and is directed to tube 138 and line 114 through Luer connectors 116 and 102 to retrograde cannula 98.

Antegrade or aortic root pressure is measured through line 118 by connection to three-way stopcock 122, to pressure sensor or transducer 189 which is connected to pressure meter 120.

Retrograde or coronary sinus pressure is measured by a separate line 124. One end of line 124 communicates with cannula 98 through line 104 and Luer connectors 106 and 126. The other end of line 124 is connected to three-way stopcock 130, to pressure sensor or transducer 187 which connects to pressure meter 128. Line 124 is physically held in valve housing 132 but is not controlled by nor is it affected by operation of valve 74.

A separate retrograde or coronary sinus pressure monitoring line is necessary since a single line used for antegrade or aortic root pressure monitoring would initially give an inaccurate reading after switching from the high pressure antegrade infusion to the lower pressure retrograde infusion.

A particular advantage of having a separate retrograde or coronary sinus pressure monitoring line is that it is possible to sense and measure the coronary sinus pressure during both antegrade and retrograde infusion.

Figure 5:
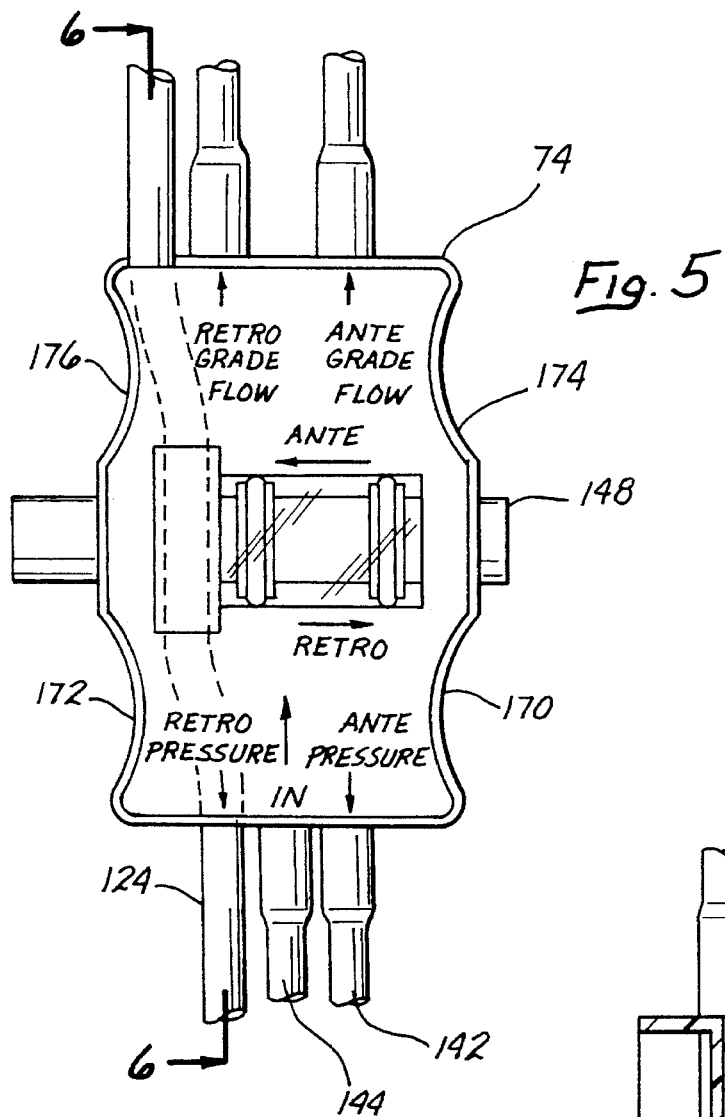
FIG. 5 shows a partially broken away elevation view of the antegrade/retrograde valve of the invention shown in FIGS. 1–4.
Figure 6:
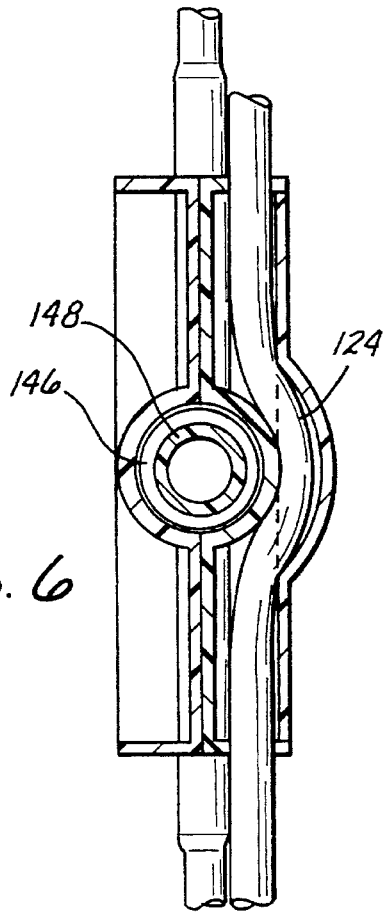
FIG. 6 shows a section taken along the lines 6—6 of FIG. 5 and details the coronary sinus or retrograde pressure measurement line.

The operation of valve 74 can be seen in better detail in FIGS. 2, 4, and 5. The valve consists of a housing 132 having a generally flattened rectangular shape with oppositely disposed curved sides 170, 172 and 174, 176. The curved sides 170, 172 and 174, 176 are ergonomically designed for ease in grasping the valve and operating it with one hand.

The valve housing 132 is formed with an upper portion 134 having integrally formed tubular passages 136 and 138.

A lower portion 140 of the housing 132 has integrally formed tubular passages 142 and 144. The tubular passages 136 and 138 of the upper portion 134 and the tubular passages 142 and 144 of the lower portion 140 of the housing 132 open interiorly into a cylindrical inner passage or chamber 146. Cylindrical inner passage or chamber 146 is disposed centrally and substantially crosswise and joins the upper portion 134 to the lower portion 140 of the valve housing 132.

Cylindrical inner passage 146 has two open ends, each of which are partially closed by a circular flange 147 and 149.

Within the central crosswise cylindrical passage 146 is a tubular member 148 which is disposed lengthwise within the tubular passage 146 for sliding lengthwise movement within passage 146. The diameter of tubular member 148 is smaller than the diameter of cylindrical passage 146 which provides a space between the interior of passage 146 and the exterior surface of tubular member 148 for passage of fluid.

The tubular member 148 is provided with three pairs of exterior, ringed flanges 150, 152, and 154. The pairs of ringed flanges 150, 152, and 154 are disposed substantially perpendicular to and are spaced apart along the lengthwise axis of tubular member 148 and divide the passage or inner chamber 146 into separate compartments or cells. The circular ringed flanges 150, 152, and 154 enclose ring gaskets 156, 158, and 160 respectively which fit between or are seated within each pair of ringed flanges.

The sliding tubular member 148 can be slid in one direction as shown in FIG. 2 until ringed flanges 150 of tubular member 148 are stopped by circular flange 149 at the open end of passage 146 for purposes of providing antegrade infusion flow. This position permits the entry of blood and cardioplegic solution from line 108 which is connected to passage 144 into a portion or compartment of the cylindrical interior passage or inner chamber 146 of housing 132.

The gaskets 158 and 160 restrict or confine the circulation of the mixture of blood and cardioplegic solution to entry into interior passage 136 within the upper portion 134 of valve 74. Interior passage 136 is connected with line 110 and antegrade cannula 92 through Luer connectors 96 and 112.

At the same time, the mixture of blood and cardioplegic solution enters passage 142 of valve 74 for measurement of antegrade or aortic root pressure. The antegrade or aortic root pressure is measured online or within the line 110 by pressure exerted in passage 142 of valve 74 and line 118 which connects with stopcock 122 and with pressure sensor or transducer 189 and pressure gauge or meter 120.

When retrograde infusion is desired, the tubular member 148 is slid in the opposite direction until ringed flanges 154 on tubular member 148 are stopped by circular flange 147 at the end of open passage 146 as shown in FIG. 4. In this instance, the entry of blood and cardioplegic solution from line 108 passes into the valve 74 through opening or passage 144 and into a portion or compartment of the interior passage or chamber 146 as defined by gaskets 156 and 158. Here the mixture is directed into line 138 of housing 132 which is connected to line 114 to retrograde cannula 98 through Luer connectors 116 and 102. Retrograde or coronary sinus pressure can be measured at all times by virtue of the separate and independent connection of line 124 to stopcock 130, pressure sensor or transducer 187 and pressure gauge 128. Line 124 passes physically within valve housing 132 but is independent of the operation of valve 74. This can be seen in greater detail in FIG. 6. Therefore, since line 124 is connected to retrograde cannula 98 through side line 104 and Luer connectors 106 and 126, it is possible to have a constant reading of the retrograde or coronary sinus pressure.

Except for the gaskets 158 and 160, the valve and tubing are preferably made of a plastic material which is clear and inert to blood and the cardioplegic solution. Clear polycarbonate has been used with success for all parts of the valve except for the gaskets and clear polyvinyl chloride has been used for the tubing.

The gaskets 156, 158, and 160 are preferably made of rubber or rubber-like material such as silicone rubber which can provide a fluid tight seal under the pressures and temperatures under which the valve 74 must operate.

Also, best results have been obtained using large bore tubing of about ⅛" in internal diameter with correspondingly sized Luer connections and stopcocks. Large bore tubing reduces pressure drop and blood hemolysis.

In addition, use of tubing which is coextruded is preferred to minimize bunching or kinking of the tubing.

The antegrade/retrograde blood cardioplegia infusion method of the invention comprises providing at least one cardioplegia solution, providing oxygenated blood, mixing at least one cardioplegic solution with the oxygenated blood to provide a mixture having predetermined ratios of blood to cardioplegic solution, pumping or otherwise delivering the mixture of the blood and cardioplegic solution through a valve selected for antegrade or for retrograde infusion, cannulating the aortic root and connecting the cannula to the valve for antegrade infusion, cannulating the coronary sinus and connecting the cannula to the valve for retrograde infusion, measuring and monitoring the antegrade infusion pressure online simultaneously with antegrade infusion through the valve, and measuring and monitoring the retrograde infusion pressure simultaneously at least with retrograde infusion and independently of the valve.

Various modifications of the invention are contemplated and can be resorted to without departing from the spirit and scope of the invention as defined by the following claims.

We claim:

1. An antegrade/retrograde cardioplegia system comprising in combination:

at least one reservoir for cardioplegic solution;

at least one reservoir for blood;

flow control means;

pump means for pumping cardioplegic solution and blood;

mixing means in communication with said pump means for mixing cardioplegic solution and blood;

heat exchange means in communication with said mixing means for heating or cooling cardioplegic solution and blood;

an antegrade/retrograde valve in communication with said mixing means;

aortic root cannula means in communication with said valve;

coronary sinus cannula means in communication with said valve;

aortic root pressure sensing means;

coronary sinus pressure sensing means;

at least one means for fluid communication between said at least one reservoir for blood, said at least one reservoir for cardioplegic solution, said pump means, said mixing means, said heat exchange means, and said antegrade/retrograde valve;

at least one means for fluid communication between said antegrade/retrograde valve and said aortic root cannula means and said coronary sinus cannula means, and, wherein said antegrade/retrograde valve comprises:

a housing having an inner chamber;

a plurality of conduits within said inner chamber comprising at least one first conduit in communication with said inner chamber and with said mixing means for introduction of cardioplegic solution and blood into said inner chamber;

at least one second conduit in communication with said inner chamber for communication with said aortic root pressure sensing means;

at least one third conduit in communication with said inner chamber for communication with said aortic root cannula means;

at least one fourth conduit in communication with said inner chamber for communication with said coronary sinus cannula means and with said coronary sinus pressure sensing means;

a sliding member disposed within said inner chamber for sliding to at least one position to provide selective fluid communication between said at least one first conduit, said at least one second conduit, and said at least one third conduit for antegrade infusion and aortic root pressure monitoring and for sliding to at least one other position to provide selective fluid communication between said at least one first conduit and said at least one fourth conduit for retrograde infusion and coronary sinus pressure monitoring.

2. A system according to claim 1 wherein said coronary sinus pressure sensing means comprises at least one fifth conduit in fluid communication with said coronary sinus cannula means, a pressure sensor in communication with said at least one fifth conduit, and a pressure meter in communication with said pressure sensor.

3. A system according to claim 2 wherein said at least one fifth conduit is held by said antegrade/retrograde valve in a manner independent of the operation of said valve.

4. A system according to claim 1 wherein said aortic root pressure sensing means comprises a pressure sensor in communication with said second conduit, and a pressure meter in communication with said pressure sensor.

5. An antegrade/retrograde valve comprising:

a housing having an inner chamber;

a plurality of conduits within said inner chamber comprising at least one first conduit in communication with said inner chamber for introduction of cardioplegic solution and blood into said inner chamber;

at least one second conduit in communication with said inner chamber for communication with a pressure sensing means for measuring aortic root pressure;

at least one third conduit in communication with said inner chamber for communication with an aortic root cannula;

at least one fourth conduit in communication with said inner chamber for communication with a coronary sinus cannula and with a pressure sensing means for measurement of coronary sinus pressure;

a sliding member disposed within said inner chamber for sliding to at least one position to provide selective fluid communication between said at least one first conduit, said at least one second conduit, and said at least one third conduit for antegrade infusion and aortic root pressure monitoring and for sliding to at least one other position to provide selective fluid communication between said at least one first conduit and said at least one fourth conduit for retrograde infusion and coronary sinus pressure monitoring; and, a fifth conduit for communication with said coronary sinus cannula means and with a pressure sensing and measuring means, wherein said fifth conduit is held by said antegrade/retrograde valve in a manner independent of the operation of said valve.

6. An antegrade/retrograde valve according to claim 5 wherein said first and second cylinders are movable along the axial direction with respect to each other whereby at least two of said conduits are included within a separate compartment.

7. An antegrade/retrograde valve according to claim 5 wherein said cylindrical members forming said inner chamber are formed of a plastic material.

8. An antegrade/retrograde valve according to claim 7 wherein said cylindrical members forming said inner chamber are formed of a clear material.

9. An antegrade/retrograde valve according to claim 5 wherein said housing is ergonomically sized for grasping and one-handed operation of the sliding member.

10. An antegrade/retrograde valve according to claim 5 wherein said conduits have a diameter of at least about ⅛".

11. An antegrade/retrograde valve comprising:

a housing having an inner chamber;

a plurality of conduits within said inner chamber comprising at least one first conduit in communication with said inner chamber for introduction of cardioplegic solution and blood into said inner chamber;

at least one second conduit in communication with said inner chamber for communication with a pressure sensing means for measuring aortic root pressure;

at least one third conduit in communication with said inner chamber for communication with an aortic root cannula;

at least one fourth conduit in communication with said inner chamber for communication with a coronary sinus cannula and with a pressure sensing means for measurement of coronary sinus pressure;

a sliding member disposed within said inner chamber for sliding to at least one position to provide selective fluid communication between said at least one first conduit, said at least one second conduit, and said at least one third conduit for antegrade infusion and aortic root pressure monitoring and for sliding to at least one other position to provide selective fluid communication between said at least one first conduit and said at least one fourth conduit for retrograde infusion and coronary sinus pressure monitoring;

said inner chamber comprises a first cylinder having axially disposed therein a second cylinder having a diameter less than the diameter of said first cylinder to define an inner chamber in the space included between said first and said second cylinders;

fluid sealing means disposed within said inner chamber for dividing said inner chamber into separate compartments along the axial length of said first cylinder;

said fluid sealing means comprises one or more gaskets disposed along the axial length of said second cylinder and sized to provide a fluid seal within said inner chamber, said gaskets dividing said inner chamber into separate compartments;

said tubular means are comprised of clear plastic flexible tubing;

said conduits are in the form of tubular nipples disposed substantially perpendicular to the axis of said first cylinder for connection with tubular means; and, a fifth conduit in the form of tubing for communication with said coronary sinus cannula means and with a pressure sensing and measuring means, wherein said fifth conduit is held within said housing in a manner independent of the operation of said valve and wherein adjacent tubing held by said valve are coextruded.

12. A method for antegrade/retrograde blood cardioplegia comprising:

providing at least one cardioplegic solution;

providing oxygenated blood;

mixing said at least one cardioplegic solution with said oxygenated blood to provide a mixture having predetermined ratios of blood to cardioplegic solution which range from all blood to all cardioplegic solution;

delivering said mixture through a valve selected for antegrade or for retrograde infusion;

cannulating the aortic root and connecting the cannula to said valve for antegrade infusion;

cannulating the coronary sinus and connecting the cannula to said valve for retrograde infusion;

measuring and monitoring the aortic root pressure at least when said antegrade infusion is taking place;

measuring and monitoring the coronary sinus pressure at least when said retrograde infusion is taking place;

said valve comprising:

a housing having an inner chamber;

a plurality of conduits comprising at least one first conduit in communication with said inner chamber for introduction of cardioplegic solution and blood into said inner chamber;

at least one second conduit in communication with said inner chamber for communication with a pressure sensor for measurement of aortic root pressure;

at least one third conduit in communication with said inner chamber for communication with an aortic root cannula;

at least one fourth conduit in communication with said inner chamber for communication with a coronary sinus cannula;

a sliding member disposed within said inner chamber for sliding to at least one position to provide selective fluid communication between said at least one first conduit, said at least one second conduit, and said at least one third conduit for antegrade cardioplegic infusion and aortic root pressure monitoring and for sliding to at least one other position to provide selective fluid communication between said first conduit and said fourth conduit for retrograde cardioplegic infusion and coronary sinus pressure monitoring.

13. A method according to claim 12 further comprising providing a separate retrograde pressure sensing conduit in fluid communication with the coronary sinus cannula and with a pressure sensor and pressure meter to provide continuous coronary sinus pressure measurement during both antegrade infusion and retrograde infusion.

14. A method according to claim 13 wherein said blood to cardioplegic solution ratio is in the range of 1 to 1 and 9 to 1.

15. A method according to claim 12 wherein at least two different cardioplegic solutions are used.

16. A method according to claim 12 wherein all cardioplegic solution is used.

17. A method according to claim 12 wherein antegrade infusion is delivered to the aortic root at a pressure no greater than about 300 mm Hg and wherein retrograde infusion is delivered to the coronary sinus at a pressure no greater than about 50 mm Hg.

18. A method according to claim 12 wherein said antegrade infusion and said retrograde infusion are delivered at a temperature in the range of about 4° C. to about 37° C.

19. A method for antegrade/retrograde blood cardioplegia comprising:

providing at least one cardioplegic solution;

providing oxygenated blood;

mixing said at least one cardioplegic solution with said oxygenated blood to provide a mixture having predetermined ratios of blood to cardioplegic solution which range from all blood to all cardioplegic solution;

delivering said mixture through a valve selected for antegrade or for retrograde infusion;

cannulating the aortic root and connecting the cannula to said valve for antegrade infusion;

cannulating the coronary sinus and connecting the cannula to said valve for retrograde infusion;

measuring and monitoring the aortic root pressure by communication with said valve during antegrade infusion; and, measuring and monitoring the coronary sinus pressure independently of said valve during both antegrade and retrograde infusion.

\* \* \* \* \*